United States Patent [19]
Takahashi et al.

[11] Patent Number: 5,334,740
[45] Date of Patent: Aug. 2, 1994

[54] CYCLOHEXANETRIOL DERIVATIVES

[75] Inventors: Takashi Takahashi, Yokohama; Manzo Shiono, Okayama, both of Japan

[73] Assignee: Kurary Co., Ltd., Okayama, Japan

[21] Appl. No.: 851,943

[22] Filed: Mar. 13, 1992

[30] Foreign Application Priority Data

Mar. 13, 1991 [JP] Japan ................... 3-073932

[51] Int. Cl.$^5$ ................. C07D 311/02; C07D 262/20; C07C 69/74
[52] U.S. Cl. ..................... 548/110; 548/241; 549/214; 549/289; 549/362; 560/126; 568/376
[58] Field of Search ............... 549/437, 362, 289, 214; 548/241, 110; 568/376; 560/126

[56] References Cited

PUBLICATIONS

CA 113(7):59732v Enantiospecific . . . cyclophellitol. Tatsuta et al., p. 759, 1990.
CA 115(19):208336q Syntheses . . . analogs. Tatsuta et al., p. 1061, 1991.

*Primary Examiner*—Mary C. Lee
*Assistant Examiner*—Joseph K. McKane
*Attorney, Agent, or Firm*—Wenderoth, Lind & Ponack

[57] ABSTRACT

Cyclohexanetriol derivatives represented by the formula

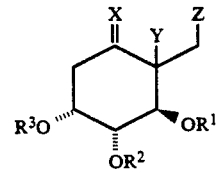

wherein
R$^1$, R$^2$ and R$^3$ are the same or different, and each denotes a hydrogen atom or a protecting group of a hydroxyl group,
X denotes an oxygen atom, =CHCH$_2$OR$^4$, =CHCHO or =CHCO$_2$R$^5$, Y denotes a hydrogen atom and Z denotes —OR$^6$, or Y and Z together form a single bond; or X and Z together form =NO—, =CHCH(OR$^7$)O— or =CHCO$_2$— and Y is a hydrogen atom, R$^4$ and R$^6$ denote a hydrogen atom or a protecting group of a hydroxyl group respectively, R$^5$ denotes a lower alkyl group, and R$^7$ denotes a hydrogen atom or a lower alkyl group.

Said derivatives are useful as synthetic intermediates of 1-hydroxyvitamin D derivatives.

9 Claims, No Drawings

CYCLOHEXANETRIOL DERIVATIVES

This invention relates to novel cyclohexanetriol derivatives. More specifically, this invention relates to $1\alpha$, $2\beta$, $3\beta$-cyclohexanetriol derivatives useful as key A-ring synthons to synthesize $1\alpha$-hydroxyvitamin D derivatives, especially $1\alpha$-hydroxyvitamin D derivatives having a substituent in the $2\beta$-position, e.g., $2\beta$-hydroxypropoxy-$1\alpha$, 25-dihydroxyvitamin $D_3$.

In recent years, with the progress of studies on vitamin D, the above $1\alpha$-hydroxyvitamin D derivatives and many other $1\alpha$-hydroxyvitamin D derivatives have been developed as medicaments. In this connection, a convergent synthesis process is useful for not only producing same but also synthesizing metaborites, decomposition products or labeled compounds which are essential in development as medicaments.

It has been proposed that $2\beta$-hydroxypropoxy-$1\alpha$, 25-dihydroxyvitamin $D_3$ which is expected to be put to practical use as an osteoporosis treating agent having high blood durability is synthesized by using asteroid compound as a starting material, epoxidizing the A-ring and then opening the epoxide ring to introduce a hydroxyalkoxy group into the 2-position [see, e.g., U.S. Pat. No. 4,666,634 (Japanese Laid-open Patent Application (Kokai) No. 267,549/1986)]. However, it suffers drawbacks that a starting material can hardly be obtained and the final step of the process is a photoreaction with a low yield.

As a convergent process for synthesizing 1-hydroxyvitamin D derivatives, there has been reported a process which comprises forming an A-ring synthon of a 1-hydroxyvitamin D derivative by using as a starting material, e.g., (S)-(+)-carvone (J. Org. Chem. 1986, 51, 3098–3108), (R)-(−)-carvone (J. Org. Chem. 1989, 54, 3515–3517), or a cyclohexenedicarboxylic acid ester (Tetrahedron Letters, vol. 31, No. 11, pp. 1577–1580, 1990), and combining it with a CD-ring synthon.

These processes have however drawbacks that the starting material is costly, reagents which are industrially hard to obtain and limited in use have to be employed, and a synthesis route up to key intermediates is long and/or intricate; they are thus not necessarily satisfactory in industrial practice.

Besides, the processes set forth in the above literature are all concerned with synthesis of a $1\alpha$-hydroxyvitamin D derivative having no substituent in the 2-position. A-ring synthons available in synthesis of $1\alpha$-hydroxyvitamin D derivatives having a substituent in the 2-position, such as 2-hydroxypropoxy-$1\alpha$, 25-dihydroxyvitamin $D_3$, have been so far unknown.

It is thus an object of this invention to provide novel cyclohexanetriol derivatives useful in synthesizing $1\alpha$-hydroxyvitamin D derivatives, especially $1\alpha$-hydroxyvitamin D derivatives having a substituent in the 2-position, which can be produced in relatively short steps using inexpensive starting materials that can easily be obtained.

According to this invention, there are provided cyclohexanetriol derivatives represented by formula (I)

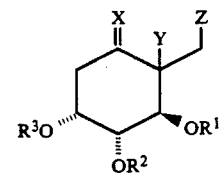

wherein $R^1$ $R^2$ and $R^3$ are the same or different, and each denotes a hydrogen atom or a protecting group of a hydroxyl group, X denotes an oxygen atom, $=CHCH_2OR^4$, $=CHCHO$ or $=CHCO_2R^5$, Y denotes a hydrogen atom and Z denotes $-OR^6$ or Y and Z together form a single bond; or X and Z together form $=NO-$, $=CHCH(OR^7)O-$ or $=CHCO_2-$ and Y is a hydrogen atom, $R^4$ and $R^6$ denote a hydrogen atom or a protecting group of a hydroxyl group respectively, $R^5$ denotes a lower alkyl group, and $R^7$ denotes a hydrogen atom or a lower alkyl group.

The cyclohexanetriol derivatives of formula (I) provided by this invention are useful as synthetic intermediates of $2\beta$-hydroxypropoxy-$1\alpha$, 25-dihydroxyvitamin $D_3$ which is expected to be clinically applied as an osteoporosis treating agent having high blood durability. They are also quite useful as synthetic intermediates of $1\alpha$-hydroxyvitamin D derivatives which are deemed effective for treating defective diseases of calcium metaborism, e.g., chronic renal failure, hypoparathyroidism, secondary hyperparathyroidism, osteomalacia and osteoporosis, such as $1\alpha$-hydroxyvitamin $D_3$, $1\alpha$, 25-dihydroxyvitamine $D_3$, $1\alpha$-hydroxyvitamin $D_2$, and 24-epi-$1\alpha$, 25-dihydroxyvitamin $D_2$, and as synthetic intermediates of $1\alpha$-hydroxyvitamin D derivatives which are expected to be effective for treating skin diseases, e.g., psoriasis and diseases caused by abnormal cell differentiation, e.g., myelogenous leukemia, such as $1\alpha$, 24-dihydroxyvitamin $D_3$, 22-oxa-1, 25-dihydroxyvitamin $D_3$, and 22-dehydro-26,27-cyclo-$1\alpha$, 24-dihydroxyvitamin $D_3$.

The word "lower" here referred to means that the number of carbon atoms of a group or a compound to which this word is applied is 6 or less, preferably 4 or less.

The protecting group of the hydroxyl group denoted by $R^1$, $R^2$, $R^3$, $R^4$ and/or $R^6$ can be any protecting group which can be removed by a protecting group eliminating means such as hydrolysis or hydrogenolysis. Examples of the protecting group are as follows.

(i) an acyl group represented by formula $R^aCO-$ [wherein $R^a$ denotes a hydrogen atom, or a $C_1-C_8$ alkyl, $C_1-C_4$ haloalkyl or aryl group], such as a formyl, acetyl, propionyl, butyryl, isobutyryl, valeryl, isovaleryl, pivaloyl, caproyl, benzoyl or trifluoroacetyl group, (ii) an alkoxycarbonyl group represented by formula $R^bOCO-$ [wherein $R^b$ denotes a lower alkyl, lower alkenyl, $C_7-C_9$ aralkyl or aryl group], such as a methoxycarbonyl, ethoxycarbonyl, propoxycarbonyl, isopropoxycarbonyl, allyloxycarbonyl, benzyloxycarbonyl or phenoxycarbonyl group, (iii) a trisubstituted silyl group represented by formula

[wherein $R^c$, $R^d$ and $R^e$ are the same or different, and each denotes a lower alkyl, aryl or $C_7$-$C_9$ aralkyl group], such as a trimethylsilyl, triethylsilyl, triisopropylsilyl, tert-butyldimethylsilyl, tert-butyldiphenylsilyl or tribenzylsilyl group, (iv) a 1-alkoxyalkyl group represented by formula

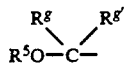

[wherein $R^5$ denotes a lower alkyl group that may optionally be substituted by a lower alkoxy group, and $R^g$ and $R^{g'}$ denote a hydrogen atom or a lower alkyl group respectively], such as a methoxymethyl, methoxyethoxymethyl, 1-ethoxyethyl or methoxyisopropyl group, and (v) a 2-oxacycloalkyl group represented by formula

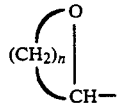

[wherein n is an integer of 3 to 6], such as a tetrahydrofuranyl or tetrahydropyranyl group.

Further, $R^1$ and $R^2$ or $R^2$ and $R^3$ may together form an acetal group represented by formula

[wherein $R^h$ and $R^i$ ore the same or different, and each denotes a hydrogen atom, or a lower alkyl, aryl or $C_7$-$C_{11}$ aralkyl group], such as an ethylidene, isopropylidene or benzylidene group.

Thus, desirous examples of the protecting group of the hydroxyl group are as follows.

$R^1$ and $R^3$: an acetyl, pivaloyl, benzoyl, methoxycarbonyl, ethoxycarbonyl, triethylsilyl, triisopropylsilyl, tert-butyldimethylsilyl, tert-butyldiphenylsilyl, methoxymethyl, methoxyethoxymethyl, 1-ethoxyethyl or tetrahydropyranyl group $R^2$: an acetyl, pivaloyl, benzoyl, methoxycarbonyl or ethoxycarbonyl group $R^4$: a tetrahydropyranyl, ethoxyethyl or methoxyisopropyl group $R^6$: a 1-ethoxyethyl, tetrahydropyranyl, methoxyisopropyl, tert-butyldimethylsilyl or triethylsilyl group Alternatively, $R^1$ and $R^2$ can together form an isopropylidene group.

Preferable examples of the protecting group of the hydroxyl group are:

$R^1$: an acetyl, tert-butyldimethylsilyl or tert-butyldiphenylsilyl group $R^2$: an acetyl or methoxycarbonyl group $R^3$: an acetyl, methoxymethyl, 1-ethoxyethyl, tert-butyldimethylsilyl or tert-butyldiphenylsilyl group $R^4$: tetrahydropyranyl group $R^6$: a tert-butyldimehtylsilyl group Alternatively, $R^1$ and $R^2$ can together form an isopropylidene group.

Meanwhile, examples of the lower alkyl group represented by $R^5$ and $R^7$ are methyl, ethyl, propyl, isopropyl, butyl, isobutyl, tert-butyl, pentyl and hexyl groups. Of these, methyl, ethyl and isopropyl groups are preferable.

Among others, the cyclohexanetriol derivatives of formula (I) wherein $R^1$ is a hydrogen atom, or an acetyl, pivaloyl, benzoyl, methoxycarbonyl, ethoxycarbonyl, triethylsilyl, triisopropylsilyl, tert-butyldimethylsilyl, tert-butyldiphenylsilyl, methoxymethyl, methoxyethoxymethyl, 1-ethoxyethyl or tetrahydropyranyl group, $R^2$ is a hydrogen atom, or an acetyl, pivaloyl, benzoyl, methoxycarbonyl or ethoxycarbonyl group, or $R^1$ and $R^2$ together form an isopropylidene group, and $R^3$ is a hydrogen atom, or an acetyl, pivaloyl, benzoyl, methoxycarbonyl, ethoxycarbonyl, triethylsilyl, triisopropylsilyl, tert-butyldimethylsilyl, tert-butyldiphenylsilyl, methoxymethyl, methoxyethoxymethyl, 1-ethoxyethyl or tetrahydropyranyl group are preferable. The cyclohexanetriol derivatives of formula (I) wherein $R^1$ is a hydrogen atom, or an acetyl, tert-butyldimethylsilyl or tert-butyldiphenylsilyl group, $R^2$ is a hydrogen atom, or an acetyl or methoxycarbonyl group, or $R^1$ and $R^2$ together form an isopropylidene group, $R^3$ is a hydrogen atom, or an acetyl, methoxymethyl, 1-ethoxyethyl, tert-butyldimethylsilyl or tert-butyldiphenylsilyl group are most preferable.

The compounds of this invention can roughly be grouped into the following three depending on the type of the substituent.

Group 1: a compound of formula (I) wherein X and Z together form =NO— and Y is a hydrogen atom, i.e., a compound of formula (IA)

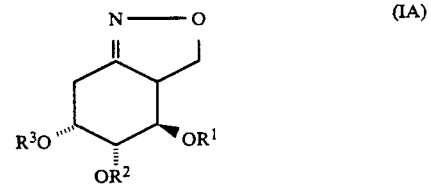

Group 2: a compound of formula (I) wherein X and Z together form =CHCH($OR^7$)O— or =CHCO$_2$—, and Y is a hydrogen atom, i.e., a compound of formula (IB) or (IC)

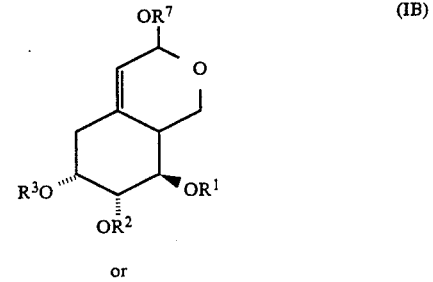

or

-continued (IC)
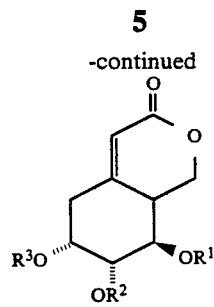

Group 3: a compound of formula (I) wherein X is an oxygen atom, =CHCH$_2$OR$^4$, =CHCHO, or =CHCO R$^5$, Y is a hydrogen atom and Z is —OR$^6$, or Y and Z together form a single bond, i.e., a compound of formula (ID) or (IE)

In the following reaction scheme A, the compound of formula (I-1) belongs to group 1, the compounds of formulas (I-6) and (I-7) to group 2, and the compounds of formulas (I-2), (I-3), (I-4), (I-5), (I-8), (I-9) and (I-10) to group 3 respectively.

The cyclohexanetriol derivatives of this invention can be produced by an industrially easy reaction according to the following reaction scheme A using an inexpensive mannitol as a starting material.

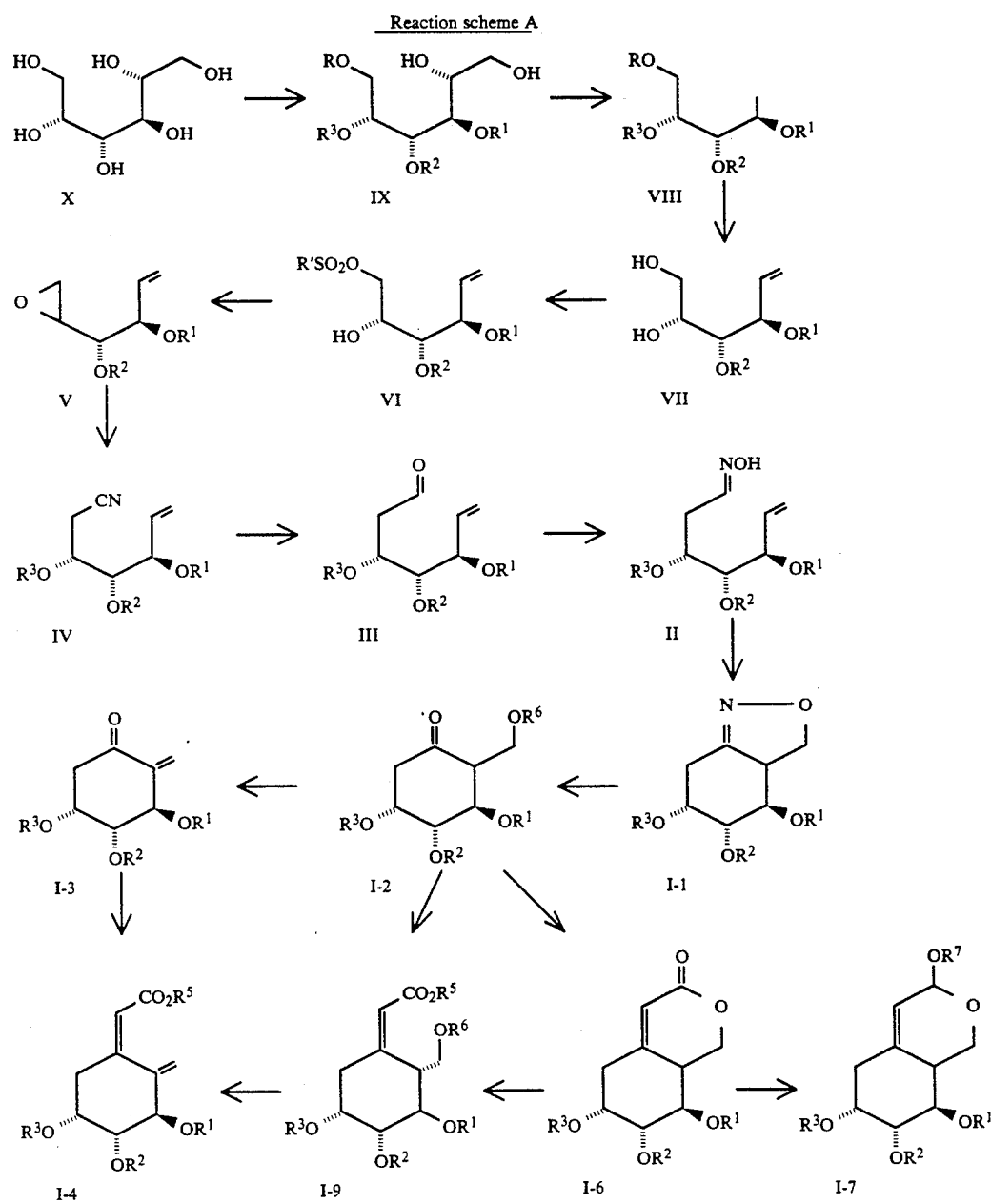

Reaction scheme A

-continued
Reaction scheme A

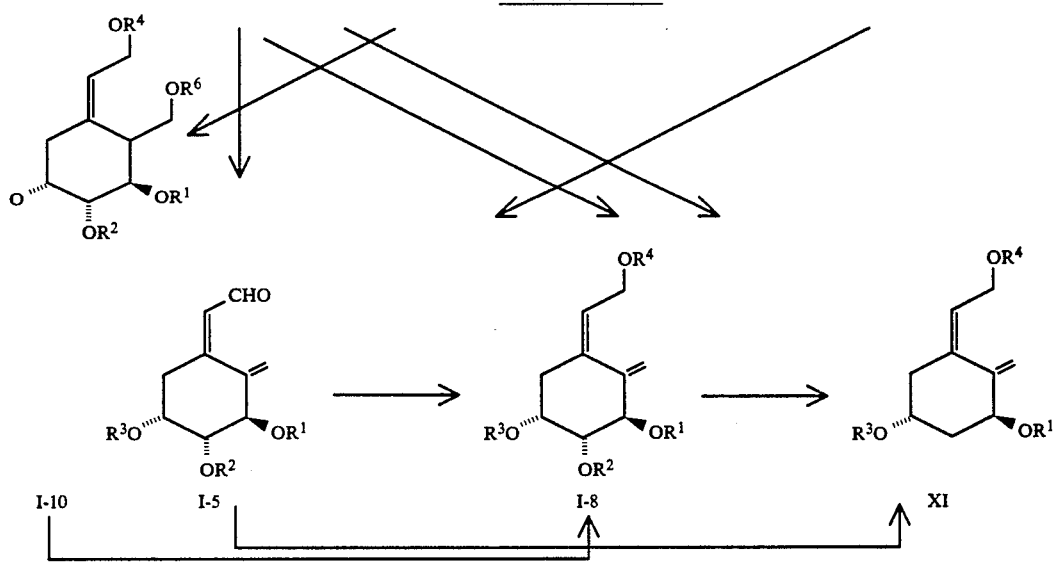

wherein $R^1$, $R^2$, $R^3$, $R^4$, $R^5$, $R^6$ and $R^7$ are as defined above, R denotes a protecting group of a hydroxyl group, and R' denotes an alkyl group (e.g., a methyl, ethyl or octyl group) or a substituted or unsubstituted aryl group (e.g., a phenyl, p-tolyl, p-chlorophenyl or naphthyl group).

The reactions in the respective steps of the above reaction scheme A will be described in more detail below.

A diol (IX) with protected hydroxyl groups in the 3-, 4-, 5- and 6-positions is formed from mannitol (X) in a usual manner. Then, said diol (IX) and 1 to 20 mols, per mol of the diol, of dimethylformamide dimethylacetal, methyl orthoformate or ethyl orthoformate are heated at a temperature ranging from room temperature to about 200° C. in the presence or absence of an acid catalyst to obtain a cyclic orthoester. To this is added, as required, 1 to 10 mols of acid anhydride such as acetic anhydride, propionic anhydride or trifluoroacetic anhydride at temperatures ranging from at room temperature to about 200° C. There is obtained a 5-hexene-1,2,3,4-tetraol derivative (VIII) with the hydroxyl groups protected.

The 5-hexene-1,2,3,4-tetraol derivative (VIII) with the hydroxyl groups protected is deprotected in a usual manner to obtain a 5-hexene-1,2,3,4-tetraol derivative (VII) with the 3- and 4-positions protected.

The 5-hexene-1,2,3,4-tetraol derivative (VII) with the 3- and 4-positions protected is converted into a 2,3,4-trihydroxy-5-hexen-1-yl monosulfonate derivative (VI) with the 3- and 4-positions protected by the reaction with 1 to 5 mols of a sulfonating agent such as p-toluenesulfonyl chloride or methanesulfonyl chloride at temperatures ranging from about −30° C. to about 80° C. in the presence of a base such as pyridine or triethylamine and in the presence or absence of an inert solvent.

The monosulfonate (VI) is converted into an epoxide in a usual manner. For example, said monotosylate is dissolved in an inert solvent such as methanol, ethanol or tetrahydrofuran, and the solution is reacted with a base such as sodium carbonate, potassium carbonate, sodium hydroxide or sodium hydride. There can result a 1,2-epoxy-5-hexene-3,4-diol derivative (V) with the 3- and 4-positions protected. Moreover, the 1,2-epoxy-5-hexene-3,4-diol derivative (V) can also be afforded by a known process using D-digitoxose or tartaric acid as a starting material [See, e.g, U. Kufner et al., Liebig's Ann. Chem., 1986, 1600–1609].

The epoxide (V) is converted into nitrile in a usual manner. For example, the epoxide is dissolved in an inert solvent such as methanol, ethanol, tetrahydrofuran or dimethylformamide, and the solution is reacted with a cyanating agent such as potassium cyanide, sodium cyanide or magnesium cyanide. If required, protection and deprotection of the hydroxyl groups are conducted. There can result 3,4,5-trihydroxy-6-heptenitrile or the substance with the hydroxyl groups protected (IV).

The obtained nitrile (IV) is, after protecting the hydroxyl groups if required, reduced with diisopropyl aluminum hydride or diisobutyl aluminum hydride in a usual manner to obtain 3,4,5-trihydroxy-6-heptenal or the substance with the hydroxyl groups protected (III).

The aldehyde (III) is reacted with hydroxylamine in a usual manner to obtain an oxime (II).

The thus obtained 3,4,5-trihydroxy-6-heptenal oxime (II) with the hydroxyl groups protected is dissolved in an inert solvent such as methylene chloride, chloroform, dichloroethane, toluene or dioxane, and the solution is reacted with 1 to 20 mols, per mol of said oxime, of an oxidizing agent such as a sodium hypochlorite aqueous solution or tert-butyl hypochlorite in the presence or absence of a catalyst such as triethylamine or pyridine at temperatures ranging from about −20° C. to about 30° C. There can result a cyclohexanetriol derivative (I-1) wherein the obtained nitrile oxide causes 1,3-dipole cycloaddition.

The cyclohexanetriol derivative (I-1) is subjected to hydrogenolysis in an inert solvent such as methanol, ethanol or tetrahydrofuran or its mixture with water with a hydrogenation catalyst such as Raney nickel, palladium-carbon or platinum oxide in a hydrogen atmosphere and if required, in the presence of an acid such as boric acid or acetic acid, and is subjected to protection of the hydroxyl groups, if required. There can be obtained a cyclohexanetriol derivative (I-2).

The cyclohexanetriol derivative (I-2) can be converted into a cyclohexanetriol derivative (I-3) by dehydration in a usual manner.

Into the cyclohexanetriol derivative (I-3) is introduced an alkoxycarbonylmethylene group in a usual manner, e.g., by a Wittig-Horner reaction, and the geometry of the double bond is isomerized from trans to cis by a photosensitization reaction. There can be obtained a cyclohexanetriol derivative (I-4).

The ester portion of the cyclohexanetriol derivative (I-4) is reduced with diisobutyl aluminum hydride in a usual manner. There can be obtained a cyclohexanetriol derivative (I-5).

Moreover, the cyclohexanetriol derivative (I-4) or the cyclohexanetriol derivative (I-5) is reduced with diisobutyl aluminum hydride, lithium aluminum hydride, bismethoxyethoxyaluminum hydride, sodium borohydride, lithium borohydride or lithium triisobutyl aluminum hydride, and the hydroxyl groups are protected if required. There can result a cyclohexanetriol derivative (I-8).

Meanwhile, the hydroxyl group in the side chain of the cyclohexanetriol derivative (I-2) is esterified with phosphinoacetic acid using dicyclohexylcarbodiimide as a condensation agent, followed by an intramolecular Wittig-Horner reaction. There can be obtained a cyclohexanetriol derivative (I-6).

The ester portion of the cyclohexanetriol derivative (I-6) is reduced with diisobutyl aluminum hydride in a usual manner, and if required, acetalized with a lower alcohol. There can be obtained a cyclohexanetriol derivative (I-7).

The cyclohexanetriol (I-7) can be converted into cyclohexanetriol (I-5) by dehydration in a solvent mixture of a water-soluble solvent such as tetrahydrofuran, dioxane, methanol or ethanol and water in the presence of p-toluenesulfonic acid, sulfuric acid or hydrochloric acid.

Further, the cyclohexanetriol derivative (I-6) is reacted in a lower alcohol with a base such as sodium hydroxide, lithium hydroxide, potassium hydroxide, barium hydroxide, sodium methoxide or sodium ethoxide, and if required, esterification and protection and deprotection of the hydroxyl groups are carried out. There can result a cyclohexanetriol derivative (I-9).

The cyclohexanetriol derivative (I-9) is dehydrated in a usual manner. There can result a cyclohexanetriol derivative (I-4). The dehydration can be conducted by a general method via sulfonation and halogenation; it can preferably be performed by a method via an organoselenium compound [see "Tetrahedron Letters", vol. 31, pp. 1577–1580 (1990)].

The cyclohexanetriol derivative (I-9) can also be afforded by reacting the cyclohexanetriol derivative (I-2) with silyl acetate and subjecting the reaction mixture to a Peterson reaction.

The ester portion of the cyclohexanetriol derivative (I-9) is reduced with a metal hydride such as lithiuim aluminum hydride or diisobutyl aluminum hydride in a usual manner and if required, the hydroxyl groups in the substance are protected. There can be obtained a cyclonexanetriol derivative (I-10).

Isolation of the thus obtained cyclohexanetriol derivative (I) [the compounds of formula (I-1) to (I-10) in the reaction scheme A] from the reaction mixture and its purification are carried out in a manner ordinarily used in an organic reaction. For example, the reaction mixture is poured into ice water, extracted with an organic solvent such as diethyl ether, washed in sequence with dilute hydrochloric acid, a sodium hydrogen carbonate aqueous solution and a sodium chloride aqueous solution in this sequence, dried and concentrated to obtain a crude product. The crude product is purified by recrystallization and/or by chromatography as required. There can resulted a cyclohexanetriol derivative (I).

The thus obtained cyclohexanetriol derivative (I-8) can be converted into a cyclohexanediol derivative (XI) by sulfonylating the hydroxyl group in the 2-position thereof with methanesulfonyl chloride, p-toluenesulfonyl chloride or benzenesulfonyl chloride in the presence of triethylamine or pyridine, and then reducing the substance with lithium aluminum hydride or lithium triethylborohydride. The cyclohexanediol derivative (XI) is a known one as an A-ring synthon for producing a 1α-hydroxyvitamin D compound. It can be converted into the aforesaid various 1α-hydroxyvitamin D derivatives having pharmaceutical activity by a method known per se [see, e.g., E. G. Baggiolini et al., J. Am. Chem. Soc., 104, 2945–2948 (1982)].

Besides, since the cyclohexanetriol derivatives of this invention have the hydroxyl groups in not only the 1- and 3-positions but also the 2-position, they can advantageously be utilized as A-ring synthons for producing 1α-hydroxyvitamin D derivatives having the substituent in the 2-position upon making use of the hydroxyl group in the 2-position. For example, 2β-hydroxypropoxy-1α, 25-dihydroxyvitamin $D_3$ represented by the formula,

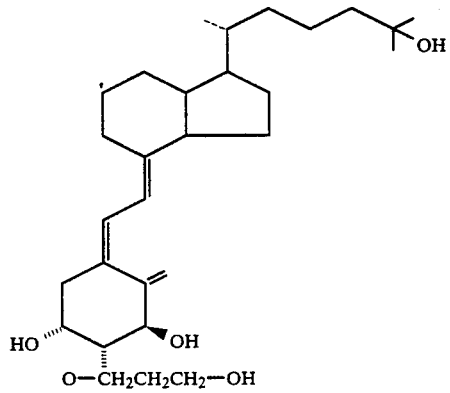

which is expected to be put to practical use as an osteoporosis treating agent having high blood durability as stated above, can be produced by introducing a 3-hydroxypropyl group into the hydroxyl group in the 2-position of the cyclohexanetriol derivative (I-8) of this invention to form a compound represented by formula (XII),

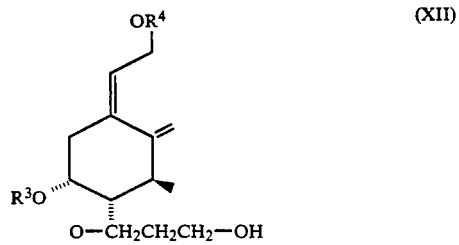

and then combining the compound with a CD ring synthon of 1α-hydroxyvitamin D₃ in a manner known per se [see, e.g., E. G. Baggiolini et al., J. Am. Chem. Soc., 104, 2945–2948 (1982)].

The following Referential Examples and Examples illustrate this invention more specifically. However, this invention is not limited thereto at all.

REFERENTIAL EXAMPLE 1

[Synthesis of 1,2:3,4-bis(dimethylmethylenedioxy)-5-hexene]

Two-hundred milliliters of N,N-dimethylformamide dimethylacetal were added to 128.5 g of 3,4:5,6-O-diisopropylidene-D-mannitol, and the mixture was heated at 100° C. to remove methanol that formed. Heating continued at 100° C. for 1 hour. After it was confirmed by thin layer chromatography that the starting material had almost disappeared, heating was conducted at 170° C., and excess N,N-dimethylformamide dimethylacetal was distilled off over about 1 hour. After the distillate disappeared, 100 ml of acetic anhydride was added gradually at 150° C. to evaporate the distillate with the distillation temperature of about 90° C. The obtained reaction mixture was cooled to room temperature, and diethyl ether was added. The organic layer was washed with a sodium chloride aqueous solution, dried over anhydrous magnesium sulfate, and then concentrated under reduced pressure. The obtained residue was purified by silica gel column chromatography to provide 60.7 g of 1,2:3,4-bis(dimethylmethylenedioxy)-5-hexene having the following properties (yield 54%).

NMR spectrum (90 MHz, CCl₄)δ: 5.90(ddd, 1H, J=5.7, 10.2, 17.2Hz), 5.13–5.52(m, 2H), 4.37(ddt, 1H, J=0.9, 5.7, 7.6 Hz), 3.8–4.2(m, 3H), 3.70(dd, 1H, J=6.6, 7.6 Hz), 1.41(s, 9H), 1.34(s, 3H).

IR spectrum (neat, cm⁻¹): 2984, 2932, 2880, 1455, 1378, 1250, 1214, 1154, 1120, 1065, 993, 924, 846, 512.

Optical rotation: [α]$_D$ = 4.18° (c=2.00, CHCl₃).

REFERENTIAL EXAMPLE 2

[Synthesis of 3,4-(dimethylmethylenedioxy)-5-hexene-1,2-diol]

Three-hundred milliliters of glacial acetic acid and 60 ml of water were added to 36.8 g of 1,2:3,4-bis(dimethylmethylenedioxy)-5-hexene obtained in Referential Example 1, and the mixture was stirred at room temperature for 14 hours. The reaction mixture was then gradually added to 500 ml of a 50% sodium hydroxide aqueous solution filled with ice. Crystals of sodium acetate formed were filtered and washed with methylene chloride. The organic layer was dried over anhydrous magnesium sulfate and concentrated under reduced pressure. The obtained residue was purified by silica gel column chromatography to afford 13.5 g of 3,4-(dimethylmethylenedioxy)-5-hexene-1,2-diol having the following properties (yield 44%).

NMR spectrum (90MHz, CCl₄)δ: 5.93(ddd, 1H, J=5.9, 9.1, 15.3HZ), 5.17–5.52(m, 2H), 4.42(dd, 1H, J=5.9, 6.4Hz), 3.5–3.9(m, 4H), 3.0–3.4(brs, 2H), 1.42(s, 6H).

IR spectrum (neat, cm⁻¹): 3414, 2984, 2930, 2878, 1727, 1645, 1455, 1428, 1407, 1371, 1250, 1214, 1168, 1120, 1055, 925,. 874, 812, 779, 734, 664, 621, 511.

Optical rotation [α]$_D$ = +4.66° (c=1.07, CHCl₃).

REFERENTIAL EXAMPLE 3

[Synthesis of 3,4-(dimethylmethylenedioxy)-2-hydroxy-5-hexen-1-yl p-toluenesulfonate]

3,4-(Dimethylmethylenedioxy)-5-hexene-1,2-diol (9.77 g) was mixed with 155 ml of pyridine and 52 ml of chloroform, and 11.39 g of p-toluenesulfonyl chloride was added gradually in four portions at 0° C. The mixture was stirred at 0° C. for 6 hours, poured into 6N hydrochloric acid with ice and extracted with diethyl ether. The extract was washed with a saturated sodium hydrogen carbonate aqueous solution and a saturated sodium chloride aqueous solution in sequence, dried with anhydrous ride aqueous solution in sequence, dried with anhydrous magnesium sulfate, and concentrated under reduced pressure to afford 17.88 g of 3,4-(dimethylmethylenedioxy)-2-hydroxy-5-hexen-1-yl p-toluenesulfonate having the following properties.

NMR spectrum (90MHz, CCl₄)δ: 7.80(d, 2H, j=8.2Hz), 7.35(d, 2H, J=8.2Hz), 5.87(ddd, H, J=6.4, 8.9, 17.3Hz), 5.15–5.49(m, 2H), 3.58–4.50(m, H), 2.45(s, 3H), 1.37(s, 6H).

IR spectrum (neat, cm⁻¹): 3508, 3084, 3064, 2984, 2932, 2882, 1647, 1597, 1494, 1453, 1369, 1308, 1291, 1213, 1174, 1118, 1096, 1063, 980, 930, 896, 873, 834, 814, 691, 664, 552, 514.

REFERENTIAL EXAMPLE 4

[Synthesis of 1,2-epoxy-3,4-(dimethylmethylenedioxy)-5-hexene]

3,4-(Dimethylmethylenedioxy)-2-hydroxy-5-hexen-1-yl p-toluenesulfonate (17.88 g) was dissolved in ml of methanol, and 17.11 g of anhydrous sodium carbonate was added at room temperature, followed by stirring the mixture for 15 minutes. The reaction mixture was filtered through Celite, and crystals were washed with diethyl ether. After the filtrate was concentrated, the solid was filtered through a silica gel column. The filtrate was concentrated under reduced pressure to obtain 7.87 g of 1,2-epoxy-3,4-(dimethylmethylenedioxy)-5-hexene having the following properties.

NHR spectrum (90MHz, CCl₄)δ: 5.90(ddd, 1H, J=6.7, 9.8, 17.2Hz), 5.2–5.52(m, 2H), 4.36(dd, 1H, J=5.4, 6.7Hz), 3.61(dd, 1H, J=5.1, 5.4Hz), 1H, J=2.6, 4.1, 4.9Hz), 2.83(dd, 1H, J=4.1, 4.9Hz), 2.70(dd, 1H, J=2.6, 4.9Hz), 1.44(s, 6Hz).

IR spectrum (neat, cm⁻¹) 3520, 2984, 2928, 1725, 1659, 1597, 1494, 1454, 1358, 1306, 1290, 1250, 1212, 1188, 1176, 1120, 1095, 1071, 1003, 919, 876, 836, 816, 778, 713, 690, 663, 571, 554.

REFERENTIAL EXAMPLE 5

[Synthesis of 4,5-(dimethylmethylenedioxy)-3-hydroxy-6-heptenenitrile]

Fifty milliliters of a saturated magnesium sulfate aqueous solution were cooled to 10° C., and 10.23 g of sodium cyanide was gradually added not to proceed over 10° C. After stirring at 10° C. for 45 minutes, a solution of 7.61 g of 1,2-epoxy-3,4-(dimethylmethylenedioxy)-5-hexene in 30 ml of methanol was gradually added to the above mixture not to proceed over 10° C. After stirring at room temperature for 2 hours, the reaction mixture was extracted with ethyl acetate. The extract was washed with a sodium chloride aqueous solution, dried over anhydrous magnesium sulfate and concentrated under reduced pressure. The obtained residue was purified by silica gel column chromatography to afford 2.11 g of 4,5-(dimethylmethylenedioxy)-3-hydroxy-6-heptenenitrile having the following properties.

NMR spectrum (90MHz, CCl$_4$)δ: 5.94(ddd, 1H, J=7.6, 10.7, 18.3Hz), 5.25–5.55(m, 2H), 4.40(dd, 1H, J=7.6, 8.0Hz), 4.08(m, 1H), 3.76(dd, 1H, J=5.8, 7.7Hz), 2.64(d, 1H, J=5.9Hz), 2.63(d, 1H, 6.4HZ), 2.46(brs, 1H), 1.42(s, 6H).

IR spectrum (neat, cm$^{-1}$): 3446, 3086, 2986, 2934, 2982, 2250, 1645, 1456, 1411, 1372, 1215, 1168, 1121, 1068, 991, 933, 873, 810, 511.

REFERENTIAL EXAMPLE 6

[Synthesis of 4,5-(dimethylmethylenedioxy)-3-methoxymethoxy-6-heptenenitrile]

Nine milliliters of diisopropylethylamine were added to 2.11 g of 4,5-(dimethylmethylenedioxy)-3-hydroxy-6-heptenenitrile, and 2 ml of methoxymethyl chloride was then added to the mixture gradually at 0° C. After stirring at 0° C. for 16 hours, the reaction mixture was diluted with 300 ml of diethyl ether, and washed with 1N hydrochloric acid, a saturated sodium hydrogen carbonate aqueous solution and a sodium chloride aqueous solution in sequence. The organic layer was dried over anhydrous magnesium sulfate, and concentrated under reduced pressure. The obtained residue was filtered by a silica gel column to afford 2.28 g of 4,5-(dimethylmethylenedioxy)-3-methoxymethoxy-6-heptenenitrile having the following properties (yield 88 %).

NMR spectrum (90MHz, CCl$_4$)δ: 5.93(ddd, 1H, J=6.3, 10.2, 17.3Hz), 5.16–5.52(m, 2H), 4.74(s, 2H), 4.35(dd, 1H, J=6.6, 7.3Hz), 3.78–4.00(m, 2H), 3.45(s, 3H), 2.60–2.80(m, 2H), 1.42(s, 6H).

IR spectrum (neat, cm$^{-1}$): 2986, 2934, 2896, 2826, 2248, 1644, 1455, 1414, 1380, 1372, 1245, 1216, 1154, 1106, 1062, 1039, 992, 920, 875, 809, 512.

REFERENTIAL EXAMPLE 7

[Synthesis of 4,5-(dimethylmethylenedioxy)-3-methoxymethoxy-6-heptenal oxime]

4,5-(Dimethylmethylenedioxy)-3-methoxymethoxy-6-heptenenitrile (159.8 mg) was dissolved in dry toluene, and 1.6 ml of 0.5N diisopropyl aluminum hydride was added at −78° C. The reaction mixture was stirred at −78° C. for 2 hours and at −40° C. for 30 minutes, and 5% dilute sulfuric acid was gradually added at 0° C. The reaction mixture was diluted with diethyl ether, and the organic layer was washed with a sodium chloride aqueous solution, dried over anhydrous magnesium sulfate, concentrated under reduced pressure to afford 91.1 mg of 4,5-(dimethylmethylenedioxy)-3-methoxymethoxy-6-heptenal.

The above 4,5-(dimethylmethylenedioxy)-3-methoxymethoxy-6-heptenal (91.9 mg) was dissolved in 1 ml of pyridine, and 45 mg of hydroxylamine hydrochloride was added at room temperature, and stirring was conducted at room temperature for 8 hours. The reaction mixture was diluted with diethyl ether. The diluted reaction mixture was washed with a saturated sodium chloride aqueous solution, dried over anhydrous magnesium sulfate, and then concentrated under reduced pressure. The obtained residue was purified by silica gel column chromatography to afford 89.5 mg of 4,5-(dimethylmethylenedioxy)-3-methoxymethoxy-6-heptenal oxime having the following properties (yield 52%).

NMR spectrum (90MHz, CCl$_4$)δ: 8.02(brs, 1H), 7.62(bs, 1H), 7.49(t, 1H, J=6.4Hz), 6.93(t, 1H, J=5.4Hz), 5.64–6.10(m, 2H), 5.16–5.00(m4H), 4.56–4.90(m, 4H), 4.24–4.48(m, 2H), 3.72–4.10(m, 4H), 3.39(s, 6H), 2.67(t, 2H, J=5.7Hz), 2.50(t, 2H, J=5.9Hz), 1.42(s, 12Hz).

IR spectrum (neat, cm$^{-1}$): 3379, 3088, 2984, 2892, 2826, 1727, 1647, 1453, 1427, 1380, 1371, 1244, 1214, 1152, 1100, 1032, 991, 920, 876, 813, 705, 665, 512, 453.

REFERENTIAL EXAMPLE 8

[Synthesis of 4,5-(dimethylmethylenedioxy)-3-(tert-butyldimethylsilyloxy)-6-heptenenitrile]

Two grams of tert-butyldimethylsilyl chloride were gradually added at 0° C. to a solution comprising 2.11 g of 4,5-(dimethylmethylenedioxy)-3-hydroxy-6-heptenenitrile, 2.0 g of imidazole and 50 ml of methylene chloride. After stirring was conducted at room temperature for 16 hours, the reaction mixture was diluted with 300 ml of diethyl ether, and washed with 1N hydrochloric acid, a saturated sodium hydrogen carbonate aqueous solution and a sodium chloride aqueous solution in sequence. The organic layer was dried over anhydrous magnesium sulfate, and concentrated under reduced pressure. The obtained residue was purified by silica gel column chromatography to afford 2.63 g of 4,5-(dimethylmethylenedioxy)-3-(tert-butyldimethylsilyloxy)6-heptenenitrile having the following properties (yield 79%).

FD mass spectrum: [M]+311.

REFERENTIAL EXAMPLE 9

[Synthesis of 4,5-(dimethylmethylenedioxy)-3-(tert-butyldimethylsilyloxy)-6-heptenal oxime]

Referential Example 7 was repeated except using 206.2 mg of 4,5-(dimethylmethylenedioxy)-3-(tert-butyldimethylsilyloxy)-6-heptenenitrile instead of 159.8 mg of 4,5-(dimethylmethylenedioxy)-3-methoxymethoxy-6-heptenenitrile. There was obtained 167 mg of 4,5-(dimethylmethylenedioxy)-3-(tert-butyldimethylsilyloxy)-6-heptenal oxime. (yield 77%).

REFERENTIAL EXAMPLE 10

[Synthesis of 4,5-(dimethylmethylenedioxy)-3-(1-ethoxyethoxy)-6-heptenenitrile]

4,5-(Dimethylmethylenedioxy)-3-hydroxy-6-heptenenitrile (3.54 g) was dissolved in 50 ml of methylene chloride under a nitrogen atmosphere, and a catalytic amount of pyridinium p-toluenesulfonate was added under ice cooling, followed by adding dropwise 2.57 ml of ethyl vinyl ether. After stirring for 2 hours, the reaction mixture was poured into a saturated sodium hydrogen aqueous solution, and extracted with diethyl ether. The organic layer was washed with a saturated sodium chloride aqueous solution. The obtained organic layer was dried over anhydrous magnesium sulfate, and concentrated under reduced pressure. The resulting residue was purified by silica gel column chromatography to provide 4.41 g of 4,5-(dimethylmethylenedioxy)-3-(1-ethoxyethoxy)-6-heptenenitrile having the following properties (yield 91%).

$^1$H-NMR spectrum (90MHz, CCl$_4$)δ: 5.7–6.1(m, 1H), 5.1–5.5(m, 2H), 4.97, 4.90(q, J=5.1Hz, 1H), 4.35(q, J=6.2Hz, 1H), 3.4–4.1(m, 2H), 3.60(q, J=6.9Hz, 2H), 2.6–2.8(m, 2H), 1.42(s, 6H), 1.34, 1.32 (d, J=5.3Hz, 3H), 1.21(t, j=7.7Hz).

REFERENTIAL EXAMPLE 11

[Synthesis of 4,5-(dimethylmethylenedioxy)-3-(1-ethoxyethoxy)-6-heptenal oxime]

4,5-(Dimethylmethylenedioxy)-3-(1-ethoxyethoxy)-6-heptenenitrile (1.40 g) was dissolved in 13 ml of dry toluene, and 2.0 ml of 2N diisobutyl aluminum hydride was added dropwise at −78° C. After stirring at −78° C. for 100 minutes, the temperature was then elevated to 0° C., and 10% dilute sulfuric acid was then gradually added. The reaction mixture was diluted with ether, and the organic layer was washed with a sodium chloride aqueous solution, dried over anhydrous magnesium sulfate, and concentrated under reduced pressure to obtain 2.61 g of 4,5-(dimethylmethylenedioxy)-3-(1-ethoxyethoxy)-6-heptenal.

The obtained 4,5-(dimethylmethylenedioxy)-3-(1-ethoxyethoxy)-6-heptenal was dissolved in 2 ml of pyridine under a nitrogen atmosphere, and 442 mg of hydroxylamine hydrochloride was added at 0° C. The mixture was stirred at room temperature for 4 hours, and the obtained reaction mixture was diluted with ether. The diluted reaction mixture was washed with a saturated sodium chloride aqueous solution, dried over anhydrous magnesium sulfate, and then concentrated under reduced pressure to afford 1.00 g of 4,5-(dimethylmethylenedioxy)-3-(1-ethoxyethoxy)-6-heptenal oxime.

REFERENTIAL EXAMPLE 12

[Synthesis of 4,5-(dimethylmethylenedioxy)-3-(tert-butyldiphenylsilyloxy)-6-heptenenitrile]

Referential Example 8 was repeated except using 3.65 of tert-butyldiphenylsilyl chloride instead of 2.0 g of tert-butyldimethylsilyl chloride to provide 4,5-(dimethylmethylenedioxy)-3-(tert-butyldiphenylsilyloxy)-6-heptenenitrile.

REFERENTIAL EXAMPLE 13

[Synthesis of 4,5-(dimethylmethylenedioxy)-3-(tert-butyldiphenylsilyloxy)-6-heptenal oxime]

Referential Example 7 was repeated except using 88 mg of 4,5-(dimethylmethylenedioxy)-3-(tert-butyldiphenylsilyloxy)-6-heptenenitrile instead of 159.8 mg of 4,5-(dimethylmethylenedioxy)-3-methoxymethoxy-6-heptenenitrile. There resulted 205 mg of 4,5-(dimethylmethylenedioxy)-3-(tert-butyldiphenylsilyloxy)-6-heptenal oxime having the following property.

FD mass spectrum: [M]$^+$453.

EXAMPLE 1

4,5-(Dimethylmethylenedioxy)-3-methoxymethoxy-6-heptenal oxime (89.5 mg) was dissolved in 4 ml of methylene chloride, and 0.035 ml of triethylamine was added at 0° C. A 10 % sodium hypochlorite aqueous solution (2.6 ml) was added at 0° C., and the mixture was stirred at 0° C. for 57 hours. The reaction mixture was diluted with diethyl ether, and washed with saturated sodium hydrogen carbonate aqueous solution and a saturated sodium chloride aqueous solution in sequence. The organic layer was dried over anhydrous magnesium sulfate, concentrated under reduced pressure, and purified by silica gel column chromatography to provide 0.0 mg of 4,5-(dimethylmethylenedioxy)-6-(methoxymethoxy)-3,3a,4,5,6,7-hexahydro-2,1-benzoisooxazole having the following properties (yield 56%).

$^1$H-NMR spectrum (90MHz, CCl$_4$, TMS)δ: 4.76(d, 1H, J=4.1Hz), 4.66(d, 1H, J=4.1Hz), 4.63(ABX, 1H, J=8.5, 10.0Hz), 4.41(ddd, 1H, J=2.3, 2.4, 3.3Hz), 4.13(ABX, 1H, J=8.5, 10.0), 3.98(dd, 1H, J=9.5, 10.0Hz), 3.63(dd, 1H, J=2.3, 9.5Hz), 3.56(ddd, 1H, J=1.3, 8.5, 10.0Hz), 3.39(s, 3H), 3.05(ABX, 1H, J=2.4, 15.7Hz), 2.41(ABXY, 1H, J=1.3, 3.3, 15.7Hz), 1.45(s, 3H), 1.44(s, 3H).

$^{13}$C-NMR spectrum (22.5MHz, CCl$_4$): 154.7, 111.4, 96.1, 80.6, 76.2, 68.8, 55.6, 53.5, 29.6, 27.0, 26.6.

IR spectrum (neat, cm$^{-1}$): 3522, 2982, 2932, 2892, 2824, 1720, 1632, 1455, 1381, 1371, 1333, 1306, 1266, 1231, 1151, 1089, 1038, 988, 918, 870, 832, 794, 780, 672, 590, 518.

EXAMPLE 2

Raney nickel W-2 ( NDHF-90: a trademark for a product of Kawaken Fine Chemical K.K.; 550 mg) was subjected to decantation once with water and once with methanol. Forty eight milligrams of boric acid were added. The atmosphere was replaced with argon and then with hydrogen. Methanol (1.5 ml) and water (0.3 ml) were added and boric acid was dissolved therein. Then, a solution of 80 mg of 4,5-(dimethylmethylenedioxy)-6-(methoxymethoxy)-3,3a,4,5,6,7-hexahydro-2,1-benzoisooxazole in 3.5 ml of methanol was added at room temperature, and the mixture was stirred for 5 hours. The reaction mixture was diluted with diethyl ether and filtered through florisel. The filtrate was washed with a saturated sodium chloride aqueous solution and dried over anhydrous magnesium sulfate. The solvent was evaporated under reduced pressure, and the obtained residue was purified by silica gel column chromatography to afford 49 mg of 2-hydroxymethyl-3,4-(dimethylmethylenedioxy)-5-(methoxymethoxy)cyclohexanone having the following properties (yield 61%).

$^1$H-NMR spectrum (90MHz, CCl$_4$, TMS) δ: 4.52–4.88(m, 2H), 4.38–4.50(m, 1H), 3.80–4.30(m, 4H), 3.36(s, 3H), 2.32–2.88(m, 4H), 1.50(s, 3H), 1.46(s, 3H)

$^{13}$C-NMR spectrum (22.5MHz, CCl$_4$): 207.8, 112.3, 96.2, 80.4, 72.8, 68.7, 59.5, 56.6, 55.6, 46.0, 27.2, 26.6, 14.7.

IR spectrum (neat, cm$^{-1}$): 3494, 2982, 2930, 2892, 1713, 1644, 1455, 1383, 1371, 1325, 1228, 1169, 1150, 1100, 1038, 999, 918, 851, 803, 787, 693, 527, 506, 439.

Optical rotation

[α]$_D$ = −7.35° (c=0.14, CHCl$_3$).

EXAMPLE 3

Pyridine (0.5 ml) was added to 22 mg of 2-hydroxymethyl-3,4-(dimethylmethylenedioxy)-5-(methoxymethoxy)cyclohexanone, and 0.1 ml of methanesulfonyl chloride was then added at 0° C., followed by stirring the mixture for 2 hours. The reaction mixture was poured into cold dilute hydrochloric acid, and extracted with diethyl ether. The extract was washed with a saturated sodium hydrogen carbonate aqueous solution and then with a saturated sodium chloride aqueous solution, dried over anhydrous magnesium sulfate, and then concentrated under reduced pressure. The obtained residue was purified by silica gel column chromatography to provide 1.8 mg of 2-methylene-3,4-(dimethylmethylenedioxy)-5-(methoxymethoxy)cyclohexanone having the following properties (yield 8.8%).

$^1$H-NMR spectrum (500MHz, CCl$_4$, TMS) δ: 5.956(dd, 1H, J=1.25, 2.75Hz), 5.497(dd, 1H, J=1.25, 2.75Hz), 4.888(dt, 1H, J=2.75, 10.08Hz), 4.831(AB, 1H, J=6.65Hz), 4.693(AB, 1H, J=6.65Hz), 4.456(ddd, 1H, J=1.37, 2.29, 18.19Hz), 3.816(dd, 1H, J=2.29, 10.08Hz), 3.387(d, 3H, J=0.91Hz), 2.814(dd, 1H, J=1.37, 18.78Hz), 2.612(dd, 1H, J=5.04, 18.78Hz), 1.522(s, 3H), 1.507(s, 3H).

IR spectrum (neat, cm$^{-1}$): 2984, 2928, 1702, 1636, 1454, 1380, 1372, 1232, 1154, 1143, 1103, 1064, 1038, 1003, 977, 946, 919, 860, 838, 806.

EXAMPLE 4

(1) Under a nitrogen atmosphere, 56.5 mg of 2-hydroxymethyl-3,4-(dimethylmethylenedioxy)-5-(methoxymethoxy)cyclohexanone and 112.3 mg of diethylphosphonylacetic acid was dissolved in 5 ml of dry diethyl ether. To this solution was added 87.9 mg of N,N'-dicyclohexylcarbodiimide at 0° C., and the mixture was stirred for 1 hour. The reaction mixture was diluted with ethyl acetate, washed with a saturated sodium chloride aqueous solution, and dried over anhydrous magnesium sulfate, and then concentrated under reduced pressure. The obtained residue was purified by silica gel column chromatography to afford 108.2 mg of (5,6-(dimethylmethylenedioxy)-4-methoxymethoxy-2-oxocyclohexyl)methyl diethylphosphonylacetate having the following properties (yield 100%).

NMR spectrum (90MHz, CCl$_4$) δ: 4.80: AB, 1H, J=6.8Hz), 4.63(AB, 1H, 6Hz), 4.0–4.5(m, 9H), 3.36(s, 3H), 2.97(d, 2H, J=21.5Hz), 2.4–3.0(m, 3H), 1.1–1.6(m, 12H).

IR spectrum (neat, cm$^{-1}$): 2982, 2932, 2628, 2524, 1737, 1666, 1476, 1445, 1371, 1240, 1163, 1100, 1027, 972, 917, 845, 787, 688, 601, 505, 439.

(2) Under a nitrogen atmosphere, 13.6 mg of (5,6-(dimethylmethylenedioxy)-4-methoxymethoxy-2-oxocyclohexyl)methyl diethylphosphonylacetate was dissolved in 1 ml of acetonitrile. At 0° C., 8.4 mg of lithium chloride and then 6 microliters of diisopropylethylamine were added, and the mixture was stirred at room temperature for 10 hours. The reaction mixture was diluted with ethyl acetate, washed with a saturated sodium chloride aqueous solution, dried over anhydrous magnesium sulfate, and concentrated under reduced pressure. The obtained residue was purified by silica gel column chromatography to afford 2.1 mg of 1,5,6,7,8,8a-hexahydro-7,8-(dimethylmethylenedioxy)-6-methoxymethoxy-3H-2-benzopyran-3-one having the following properties (yield 23%).

NMR spectrum (90MHz, CCl$_4$) δ: 5.9(brs, 1H), 3.0–5.0(m, 10H), 2.0–3.0(m, 3H), 1.3–1.5(m, 6H).

EXAMPLE 5

Under an argon atmosphere, 18 microliters of diisobutyl aluminum hydride (0.5N toluene solution) was added at −78° C. to a 0.5 ml toluene solution of 2.1 mg 1,5,6,7,8,8a-hexahydro-7,8-(dimethylmethylenedioxy)-6-methoxymethoxy-3H-2-benzopyran-3-one, and stirring was conducted for 2 hours. After the temperature was elevated to 0° C., the reaction mixture was diluted with diethyl ether, and a saturated sodium sulfate aqueous solution was added until a white precipitate was formed. To the obtained reaction mixture was added ethyl acetate, and the organic layer was washed with a saturated sodium chloride aqueous solution and dried over anhydrous magnesium sulfate, and then concentrated under reduced pressure. The obtained residue was purified by silica gel column chromatography to afford 3.8 mg of 1,5,6,7,8,8a-hexahydro-7,8-(dimethylmethylenedioxy)-6-methoxymethoxy-3H-2-benzopyran-3-ol having the following properties (yield 100%).

NMR spectrum (90MHz, CCl$_4$) δ: 5.62(brs, 1H), 5.22(brs, 1H), 4.5–4.8(m, 2H), 3.0–4.5(m, 6H), 3.3(s, 3H), 1.8–2.7(m, 3H), 1.4(s, 6H).

EXAMPLE 6

1,5,6,7,8,8a-Hexahydro-7,8-(dimethylmethylenedioxy)-6-methoxymethoxy-3H-2-benzopyran-3-ol (3.8 mg) was dissolved in 0.6 ml of dry methanol, and a catalytic amount of p-toluenesulfonic acid was added at room temperature. After the mixture was stirred at room temperature for 2 hours, triethylamine was added, and concentrated with water cooling under reduced pressure. The obtained residue was purified through a short silica gel column to provide 1.3 mg of 1,5,6,7,8,8a-hexahydro-6-methoxymethoxy-3-methoxy-3H-2-benzopyran-7,8-diol having the following properties (yield 68%).

NMR spectrum (300MHz, CCl$_4$) δ: 5.0–5.66(m, 2H), 4.55–4 85(m,2H), 3.15–4.25(m, 8H), 3.39–3.43(m, 6H), 1.95–2.80(m, 4H).

EXAMPLE 7

1,5,6,7,8,8a-Hexahydro-7,8-(dimethylmethylenedioxy)-6-methoxymethoxy-3H-2-benzopyran-3-one (28.4 mg) was dissolved in 5 ml of methanol, and 0.1 ml of a 6N sodium hydroxide aqueous solution was added under ice cooling, followed by stirring the mixture at room temperature for 2 hours. The reaction mixture was diluted with diethyl ether and neutralized with dilute hydrochloric acid under ice cooling. The organic layer was washed with a saturated sodium chloride aqueous solution and dried over anhydrous sodium sulfate. Diazomethane was blown into the solution. After excess diazomethane was evaporated, the solvent was evaporated under reduced pressure, and the residue was purified by silica gel column chromatography to provide 25.4 mg of methyl ((2-hydroxymethyl-3,4-(dimethylmethylenedioxy)-5-methoxymethoxy)cyclohexylidene)acetate having the following property (yield 80%).

FD mass spectrum: [M]+284.

EXAMPLE 8

Methyl ((2-hydroxymethyl-3,4-(dimethylmethylenedioxy)-5-methoxymethoxy)cyclohexylidene)acetate (31.6 mg) and 27.2 mg of o-nitrobenzeneselenyl cyanide were dissolved in 5 ml of tetrahydrofuran, and a solution of 24.2 mg tributylphosphine in 5 ml tetrahydrofuran was added, followed by stirring the mixture at room temperature for 1 hour. The reaction mixture was concentrated under reduced pressure, and purified by silica gel column chromatography to obtain 440 mg of methyl (2-(o-nitrobenzeselenenylmethyl)-3,4-(dimethylmethylenedioxy)-5-methoxymethoxy)cyclohexylideneacetate. Then, this product was dissolved in tetrahydrofuran, and one drop (about 0.05 ml) of a 30% aqueous hydrogen peroxide solution was added under ice cooling. The mixture was stirred at room temperature for 3 hours. The obtained reaction mixture was diluted with diethyl ether, washed with a sodium thiosulfate aqueous solution and a sodium chloride aqueous solution, and dried over anhydrous sodium sulfate, concentrated under reduced pressure and then purified by silica gel column chromatography to provide 188 mg of methyl ((2-methylene-3,4-(dimethylmethylenedioxy)-5-methoxymethoxy)cyclohexylidene)acetate having the following property (yield 63%).

FD mass spectrum: [M]+298.

EXAMPLE 9

Methyl ((2-methylene-3,4-(dimethylmethylenedioxy)-5-methoxymethoxy)cyclohexylidene)acetate (29.8 mg) was dissolved in 5 ml of toluene, and 0.4 ml of diisobutyl aluminum hydride (1M hexane solution) was added dropwise at −78° C. After the temperature was raised to 0° C., the reaction mixture was diluted with diethyl ether. A saturated sodium sulfate aqueous solution was added dropwise until a white precipitate was formed, and the mixture was filtered through Celite. The filtrate was dried over anhydrous sodium sulfate, and then concentrated. The obtained residue was purified by silica gel column chromatography to provide 25.4 mg of ((2-methylene-3,4-(dimethylmethylenedioxy)-5-methoxymethoxy)cyclohexylidene)ethanol having the following property (yield 94%).

FD mass spectrum: [M]+270.

EXAMPLE 10

Methyl ((2-methylene-3,4--(dimethylmethylenedioxy)-5-methoxymethoxy)cyclohexylidene)acetate (29.8 mg) was dissolved in 5 ml of toluene, and 0.15 ml of diisobutyl aluminum hydride (1M hexane solution) was added at −78° C. The mixture was stirred for 30 minutes, and water was added to the mixture. After the temperature was raised to 0° C., the reaction mixture was diluted with diethyl ether. A saturated sodium sulfate aqueous solution was added dropwise until a white precipitate was formed, and the mixture was filtered through Celite. The filtrate was dried over anhydrous sodium sulfate, and then concentrated. The obtained residue was purified by silica gel column chromatography to provide 15.0 mg of ((2-methylene-3,4-(dimethylmethylenedioxy)-5-methoxymethoxy)cyclohexylidene)acetaldehyde having the following property (yield 56%).

EXAMPLE 11

((2-Methylene-3,4-(dimethylmethylenedioxy)-5-methoxymethoxy)cyclohexylidene)acetaldehyde (26.8 mg) was dissolved in 2 ml of ethanol, and 3 mg of sodium borohydride was added under ice cooling. After stirring the mixture for 30 minutes, diethyl ether and dilute hydrochloric acid were added to the mixture. The organic layer was washed with a saturated sodium chloride aqueous solution, dried over anhydrous sodium sulfate, and concentrated under reduced pressure. The product was purified by silica gel column chromatography to obtain 25.4 mg of ((2-methylene-3,4-(dimethylmethylenedioxy)-5-methoxymethoxy)cyclohexylidene)ethanol (yield 94%).

EXAMPLE 12

Example 1 was followed except that 113.7 mg of 4,5-(dimethylmethylenedioxy)-3-(tert-butyldimethylsilyloxy)-6-heptenal oxime was used instead of 89.5 mg of 4,5-(dimethylmethylenedioxy)-3-methoxymethoxy-6-heptenal oxime to obtain 62.4 mg of 4,5-(dimethylmethylenedioxy)-6-(tert-butyldimethylsilyloxy)-3,3a,4,5,6,7-hexahydro-2,1-benzoisooxazole having the following property (yield 55%).

1,5,6,7,8,8a-Hexahydro-7,8-(dimethylmethylenedioxy)-6-methoxymethoxy-3H-2-benzopyran-3-one (284 mg) was dissolved in 50 ml of methanol and 5 ml of water, and a catalytic amount of p-toluenesulfonic acid was added. The mixture was refluxed for 1 hour. After cooling, the reaction mixture was poured into a sodium hydrogen carbonate aqueous solution and extracted with diethyl ether. The extract was washed with a sodium chloride aqueous solution, dried, and concentrated under reduced pressure. The product was purified by silica gel column chromatography to obtain 114 mg of 1,5,6,7,8,8a-hexahydro-6,7,8-trihydroxy-3H-2-benzopyran-3-one having the following property (yield 57%).

FD mass spectrum: [M]+200.

EXAMPLE 14

One hundred milligrams of 1,5,6,7,8,8a-hexahydro-6,7,8-trihydroxy-3H-2-benzopyran-3-one were dissolved in 10 ml of methylene chloride, and 300 mg of pyridine and 300 mg of acetyl chloride were added at room temperature, followed by stirring the mixture overnight at room temperature. The reaction mixture was diluted with ethyl acetate, washed with dilute hydrochloric acid, a sodium hydrogen carbonate aqueous solution and a sodium chloride aqueous solution in sequence, and dried over anhydrous magnesium sulfate, and then concentrated under reduced pressure. The product was purified by silica gel column chromatography to obtain 143 mg of 1,5,6,7,8,8a-hexahydro-6,7,8-triacetoxy-3H-2-benzopyran-3-one (yield 88%).

EXAMPLE 15

4,5-(Dimethylmethylenedioxy)-6-(methoxymethoxy)-3,3a,4,5,6,7-hexahydro-2,1-benzoisooxazole (257 mg) was dissolved in 10 ml of tetrahydrofuran, and 1 ml of 1N hydrochloric acid was added, followed by stirring the mixture at room temperature for 4 hours. The reaction mixture was diluted with diethyl ether, and neutralized with a sodium hydrogen carbonate aqueous solution. The organic layer was washed with a sodium chloride aqueous solution, dried over anhydrous sodium sulfate, and concentrated under reduced pressure. The obtained residue was purified by silica gel column chromatography to afford 167 mg of 4,5-dihydroxy-6-(methoxymethoxy)-3,3a,4,5,6,7-hexahydro-2,1-benzoisooxazole having the following property (yield 77%).

FD mass spectrum: [M]+217.

EXAMPLE 16

4,5-Dihydroxy-6-(methoxymethoxy)-3,3a,4,5,6,7-hexahydro-2,1-benzoisooxazole (217 mg) was dissolved in 10 ml of methylene chloride, and 1 ml of pyridine and then 100 mg of methyl chlorocarbonate were added under ice cooling. The mixture was stirred at room temperature for 3 hours. The reaction mixture was diluted with diethyl ether, washed with dilute hydrochloric acid, a sodium hydrogen carbonate aqueous solution and a sodium chloride aqueous solution in sequence. The organic layer was dried over anhydrous sodium sulfate, and concentrated was under reduced pressure. The obtained residue was purified by silica gel column chromatography to give 137 mg of 4-hydroxy-5-methoxycarbonyloxy-6-(methoxymethoxy)-

3,3a,4,5,6,7-hexahydro-2,1-benzoisooxazole having the following property (yield 50%).

FD mass spectrum: [M]+275.

EXAMPLE 17

4-Hydroxy-5-methoxycarbonyloxy-6-(methoxymethoxy)-3,3a,4,5,6,7-hexahydro-2,1-benzoisooxazole (275 mg) was dissolved in 10 ml of methylene chloride, and 200 mg of imidazole and 226 mg of tert-butyldimethylsilyl chloride were added, followed by stirring the mixture overnight at room temperature. The reaction mixture was diluted with diethyl ether, and washed with dilute hydrochloric acid, a sodium hydrogen carbonate aqueous solution and a sodium chloride aqueous solution in sequence. The organic layer was dried over anhydrous sodium sulfate, and concentration was effected under reduced pressure. The obtained residue was purified by silica gel column chromatography to give 285 mg of 4-(tert-butyldimethylsilyloxy)-5- methoxycarbonyloxy-6-(methoxymethoxy)-3,3a,4,5,6,7-hexahydro-2,1-benzoisooxazole having the following property (yield 73%).

FD mass spectrum: [M]+389.

EXAMPLE 18

4,5-(Dimethylmethylenedioxy)-6-(tert-butyldimethylsilyloxy)-3,3a,4,5,6,7-hexahydro-2,1-benzoisooxazole (327 mg) was dissolved in 10 ml of tetrahydrofuran, and 1 ml of 1N hydrochloric acid was added, followed by stirring the mixture at room temperature for 4 hours. The reaction mixture was diluted with diethyl ether, and neutralized with a sodium hydrogen carbonate aqueous solution. The organic layer was washed with a sodium chloride aqueous solution, dried over anhydrous sodium sulfate, and concentrated under reduced pressure. The obtained residue was purified by silica gel column chromatography to give 196 mg of 4,5-dihydroxy-6-(tert-butyldimethylsilyloxy)-3,3a,4,5,6,7-hexahydro-2,1-benzoisooxazole having the following property (yield 68%).

FD mass spectrum: [M]+289.

EXAMPLE 19

4,5-Dihydroxy-6-(tert-butyldimethylsilyloxy)-3,3a,4,5,6,7-hexahydro-2,1-benzoisooxazole (287 mg) was dissolved in 10 ml of methylene chloride, and 200 mg of imidazole and 226 mg of tert-butyldimethylsilyl chloride were added under ice cooling, followed by stirring the mixture overnight at room temperature. The reaction mixture was diluted with diethyl ether, washed with dilute hydrochloric acid, a sodium hydrogen carbonate aqueous solution and a sodium chloride aqueous solution in sequence, and concentrated under reduced pressure. The obtained residue was purified by silica gel column chromatography to give 265 mg of 4,6-bis(tert-butyldimethylsilyloxy)-5-hydroxy-3,3a,4,5,6,7-hexahydro-2,1-benzoisooxazole having the following property (yield 66%).

FD mass spectrum: [M]+401.

EXAMPLE 20

4,6-Bis(tert-butyldimethylsilyloxy)-5-hydroxy-3,3a,4,5,6,7-hexahydro-2,1-benzoisooxazole (401 mg) was dissolved in 20 ml of methylene chloride. Five milliliters of triethylamine and 0.5 g of 4-dimethylaminopyridine were added, and 100 mg of acetyl chloride was then added, followed by stirring the mixture overnight at room temperature. The reaction mixture was diluted with diethyl ether, and washed with dilute hydrochloric acid, a sodium hydrogen carbonate aqueous solution and a sodium chloride aqueous solution in sequence. The organic layer was dried over anhydrous sodium sulfate, and concentrated under reduced pressure. The obtained residue was purified by silica gel column chromatography to give 355 mg of 5-acetoxy-4,6-bis(tert-butyldimethylsilyloxy)-3,3a,4,5,6,7-hexahydro-2,1-benzoisooxazole having the following property (yield 80%).

FD mass spectrum: [M]+443

EXAMPLE 21

Example 2 was repeated except that 5-acetoxy-4,6-bis(tert-butyldimethylsilyloxy)-3,3a,4,5,6,7- hexahydro-2,1-benzoisooxazole was used instead of 4,5-(dimethylmethylenedioxy)-6-methoxymethoxy-3,3a,4,5,6,7-hexahydro-2,1-benzoisooxazole to give 4-acetoxy-3,5-bis(tert-butyldimethylsilyloxy)-2-hydroxymethylcyclohexanone having the following property (yield 72%).

FD mass spectrum: [M]+446.

EXAMPLE 22

Example 4 was repeated except that 4-acetoxy-3,5-bis(tert-butyldimethylsilyloxy)-2-hydroxymethylcyclohexanone was used instead of 2-hydroxymethyl-3,4-dimethylmethylenedioxy)-5-(methoxymethoxy)cyclohexanone to give 7-acetoxy-6,8-bis(tert-butyldimethylsilyloxy)-1,5,6,7,8,8a-hexahydro-3H-2-benzopyran-3-one having the following property (yield 34%).

FD mass spectrum: [M]+470.

EXAMPLE 23

Example 7 was repeated except that 7-acetoxy-6,8-bis(tert-butyldimethylsilyloxy)-1,5,6,7,8,8a-hexahydro-3H -2-benzopyran-3-one was used instead of 1,5,6,7,8,8a-hexahydro-7,8-(dimethylmethylenedioxy)-6-methoxymethoxy-3H-2-benzopyran-3-one to give methyl ((3,5-bis(tert-butyldimethylsilyloxy)-4-hydroxy-2-hydroxymethyl)cyclohexylidene)acetate having the following property (yield 81%).

FD mass spectrum: [M]+460.

EXAMPLE 24

Example 8 was repeated except that methyl ((3,5-bis(tert-butyldimethylsilyloxy)-4-hydroxy-2-hydroxymethyl)cyclohexylidene)acetate was used instead of methyl ((2-hydroxymethyl-3,4-(dimethylmethylenedioxy)-5-methoxy methoxy)cyclohexylidene)acetate to give methyl ((3,5-bis(tert-butyldimethylsilyloxy)-4-hydroxy-2-methylene)cyclohexylidene)acetate having the following property (yield 51%).

FD mass spectrum: [M]+442.

EXAMPLE 25

Methyl ((3,5-bis(tert-butyldimethylsilyloxy)-4-hydroxy-2-methylene)cyclohexylidene)acetate (442 mg) was dissolved in 20 ml of methylene chloride, and 1 ml of pyridine, a catalytic amount of 4-dimethylaminopyridine and then 150 mg of methanesulfonyl chloride were added, followed by stirring the mixture at room temperature for 4 hours. The reaction mixture was diluted with diethyl ether, and washed with dilute hydrochloric acid, a sodium hydrogen carbonate aqueous solution and a sodium chloride aqueous solution in sequence. The organic layer was dried over anhydrous sodium sulfate, and concentrated under reduced pressure. The obtained residue was purified by silica gel column chromatography to give methyl ((3,5-bis(tert-butyldimethylsilyloxy)-4-(p-methanesulfonyloxy)-2-methylene)cyclohexylidene)acetate having the following property.

FD mass spectrum: [M]+520.

REFERENTIAL EXAMPLE 14

Methyl ((3,5-bis(tert-butyldimethylsilyloxy)-4-(p-methanesulfonyloxy)-2-methylene)cyclohexylidene)acetate (52 mg) was dissolved in 10 ml of tetrahydrofuran, and 1 ml of a 1M tetrahydrofuran solution of lithium triisobutyl borohydride was added dropwise, followed by stirring the mixture at room temperature for 6 hours. To the reaction mixture was added ethyl acetate gradually, and dilute hydrochloric acid was then added. The mixture was extracted with diethyl ether. The extract was washed with a sodium chloride aqueous solution, dried over anhydrous sodium sulfate, and concentrated under reduced pressure. The obtained residue was purified by silica gel column chromatography to give 35 mg of (2-(3,5-bis(tert-butyldimethylsilyloxy)-2-methylene)cyclohexylidene)ethanol having the following properties. The spectrum data coincided with those of the literature.

Melting point: 69° C.
Optical rotation: $[\alpha]_D^{25}+7.9°$ (c=0.4, ethanol).

EXAMPLE 26

One gram of 4,5- (dimethylmethylenedioxy) -3-(1-ethoxyethoxy)-6-heptenal oxime was dissolved in 15 ml of methylene chloride, and 0.2 ml of triethylamine was added at 0° C. Then, 8 ml of a 10% sodium hypochlorite aqueous solution was added, and the mixture was stirred at 0° C. for 11 hours. The reaction mixture was diluted with ethyl ether, and washed with a sodium hydrogen carbonate aqueous solution and a saturated sodium chloride aqueous solution in sequence. The organic layer was dried over anhydrous magnesium sulfate, and concentrated under reduced pressure. The obtained residue was purified by silica gel column chromatography to give 530 mg of 4,5-(dimethylmethylenedioxy)-6-(1-ethoxyethoxy)-3,3a,4,5,6,7-hexahydro-2,1-benzoisooxazole having the following properties.

$^1$H-NMR spectrum (90MHz, CCl$_4$)δ: 4.8–5.0(m, 1H), 4.38–4.8(m, 2H), 3.2–4.38(m, 5H), 3.07, 3.08(dd, 1H, 2.6, 4.6Hz), 2.2–2.6(m, 1H), 1.44(s, 3H), 1.42(s, 3H), 1.31(d, J=5.5Hz, 3H), 1.19(t, J=7.0Hz, 3H).

EXAMPLE 27

Raney nickel W-2 (NDHF-90: a trademark for a product of Kawaken Fine Chemical K.K.; 5.98 g) was charged in a flask and decanted once with water and once with methanol. To this was added 888 mg of boric acid, and the atmosphere was replaced with argon and then with hydrogen. Methanol (25 ml) and water (6 ml) were added and boric acid was dissolved therein. Then, a solution of 4,5-(methylenedioxy)-6-(1-ethoxyethoxy)-3,3a,4,5,6,7-hexahydro-2,1-benzoisooxazole (2.03 g) in 5 ml of methanol, was added at room temperature. The mixture was stirred for 13 hours. The reaction mixture was diluted with diethyl ether, and filtrated through florisil. The filtrate was washed with a saturated sodium chloride aqueous solution, then dried over anhydrous magnesium sulfate, and concentrated under reduced pressure. The obtained residue was purified by silica gel column chromatography to afford 1.39 g of 2-hydroxymethyl-3,4-dimethylmethylenedioxy)-5-(1-ethoxyethoxy)cyclohexanone having the following properties.

$^1$H-NMR spectrum (90MHz, CCl$_4$) δ: 4.8–5.0(m, 1H), 4.45(m, 1H), 3.8–4.3(m, 4H), 3.3–3.8(m, 2H), 2.3–2.9(m, 4H), 1.49(s, 3H), 1.30(d, J=5.5Hz, 3H), 1.18(t, J=7.0Hz, 3H).

EXAMPLE 28

2-Hydroxymethyl-3,4-(dimethylmethylenedioxy)-5-(1-ethoxyethoxy)cyclohexanone (765 mg) was dissolved in 7 ml of dry methylene chloride, and 1.2 ml of triethylamine, 55.6 mg of N,N-dimethylaminopyridine and 520 mg of tert-butyldimethylsilyl chloride were added at 0° C., followed by stirring the mixture at 0° C. for 13 hours. The obtained reaction mixture was poured into 1N hydrochloric acid, and extracted with diethyl ether. The extract was washed with a saturated sodium hydrogen carbonate aqueous solution and then with a saturated sodium chloride aqueous solution, and dried over anhydrous magnesium sulfate, and then concentrated under reduced pressure. The obtained residue was purified by silica gel column chromatography to give 1.04 g of 2-(tert-butyldimethylsilyloxymethyl)-3,4-(dimethylmethylenedioxy)-5-(1-ethoxyethoxy)cyclohexanone having the following properties.

$^1$H-NMR spectrum (90MHz, CCl$_4$) δ: 4.8–5.02(m, 1H), 4.3–4.6(m, 2H), 4.0–4.3(m, 1H), 3.4–4.0(m, 4H), 2.2–2.9(m, 3H), 1.49(s, 3H), 1.45(s, 3H), 1.29(d, J=5.3Hz, 3H), 1.18(t, J=7.0Hz, 3H), 0.87(s, 9H), 0.07(s, 6H).

EXAMPLE 29

Under an atmosphere of argon, 0.80 ml of dicyclohexylamine was dissolved in 7 ml of dry tetrahydrofuran, and a hexane solution (1.63N, 3.96 mmol) of butyl lithium was added at −20° C., followed by stirring for 30 minutes. After the mixture was cooled to −78° C., 0.73 ml of ethyl trimethylsilylacetate was added, and stirred at −78° C. for 1 hour. 2-(Tert-butyldimethylsilyloxymethyl)-3,4-(dimethylmethylenedioxy)-5-(1-ethoxyethoxy)cyclohexanone (802 mg) was dissolved in 6 ml of dry tetrahydrofuran, and the solution was added dropwise at −78° C. After stirring for 2 hours at −78° C., the mixture was further stirred at 0° C. for 5 minutes, and the reaction mixture was poured into 1N hydrochloric acid with ice. The mixture was extracted with diethyl ether. The extract was washed with a saturated sodium hydrogen carbonate aqueous solution and a saturated sodium chloride aqueous solution in sequence, and then dried over anhydrous magnesium sulfate, and then concentrated under reduced pressure. The obtained residue was purified by silica gel column chromatography to give 704 mg of ethyl (2-(tert-butyldimethylsilyloxymethyl)-3,4-(diemthylmethylenedioxy)-5-(1-ethoxyethoxy)cyclohexylidene) acetate having the following properties. The starting 2-(tert-butyldimethylsilyloxymethyl)-3,4-(dimethylmethylenedioxy)-5-(1-ethoxyethoxy)cyclohexanone (227 rag) was recovered.

$^1$H-NMR spectrum (90MHz, CCl$_4$) δ: 5.73(s, 1H), 4.7–5.0(m, 1H), 4.14(q, J=7.3Hz, 2H), 3.2–3.8(m, 4H), 2.69(bddd, J=1.0, 1.5, 6.7Hz, 2H), 1.42(s, 6H), 1.29(d, J=5.3Hz, 3H), 1.26(t, J=7.3Hz, 3H), 0.88(s, 9H), 0.12(s, 3H), 0.05(s, 3H)

EXAMPLE 30

Two grams of ethyl (2-(tert-butyldimethylsilyloxymethyl)-3,4-(dimethylmethylenedioxy)-5-(1-ethoxythoxy) cyclohexylidene)acetate were dissolved in 10 ml of dry toluene, and 4.7 ml of diisobutyl aluminum hydride (2N hexane solution, 9.4 mmol) was added at −78° C., followed by stirring the mixture for 3 hours. After stirring at 0° C. for 5 minutes, a 10% sulfuric acid aqueous solution was added gradually until the reaction mixture became white. The reaction mixture was extracted with diethyl ether. The extract was washed with a sodium hydrogen carbonate aqueous solution and a saturated sodium chloride aqueous solution in sequence. The organic layer was dried over anhydrous magnesium sulfate, and concentration was effected under reduced pressure. The obtained residue was purified by silica gel column chromatography to give 1.47 g of (2-(tert-butyldimethylsilyloxymethyl)-3,4-(dimethylmethylenedioxy)-5-(1-ethoxyethoxy)cyclohexylidene) ethanol having the following properties.

$^1$H-NMR spectrum (90MHz, CCl$_4$) δ: 5.64(bt, J=6.8Hz, 1H), 4.7–4.9(m, 1H), 3.08–4.4(m, 7H), 3.48(q, J=7Hz, 2H), 2.0–3.08(m, 3H), 1.41(s, 6H), 1.20(t, J=7.0Hz, 3H), 1.04–1.4(m, 3H), 0.90(s, 9H), 0.08(s, 6H).

EXAMPLE 31

Example 26 was followed except that 1.58 g of 4,5-(dimethylmethylenedioxy)-3-(tert-butyldiphenylsilyloxy)-6-heptenal oxime was used instead of 1.00 g of 4,5-(dimethylmethylenedioxy)-3-(1-ethoxyethoxy)-6-heptenal oxime to give 1.21 g of 4,5-(dimethylmethylenedioxy)-6-(tert-butyldiphenylsilyloxy)-3,3a,4,5,6,7-hexahydro -2,1-benzoisooxazole having the following property.

FD mass spectrum: [M]+451.

EXAMPLE 32

Ethyl 2-(tert--butyldimethylsilyloxymethyl)-3,4-(dimethylmethylenedioxy)-5-(1-ethoxyethoxy)cyclohexylidene)acetate (0.472 g) was dissolved in 5 ml of tetrahydrofuran, and 3 ml of a 1M tetrabutylammonium fluoride-tetrahydrofuran solution was added, followed by stirring the mixture overnight at room temperature. The reaction mixture was diluted with diethyl ether, and washed with a saturated sodium hydrogen carbonate aqueous solution and a saturated sodium chloride aqueous solution in sequence. The organic layer was dried over anhydrous magnesium sulfate, and concentrated under reduced pressure. The obtained residue was purified by silica gel column chromatography to give ethyl (2-hydroxymethyl-3,4-(dimethylmethylenedioxy)-5-(1-ethoxyethoxy)cyclohexylidene acetate.

The obtained ethyl (2-hydroxymethyl-3,4-(dimethylmethylenedioxy)-5-(1-ethoxyethoxy)cyclohexylidene-)acetate was dissolved in 5 ml of pyridine, and 0.12 g of methanesulfonyl chloride was added, followed by stirring the mixture overnight at room temperature. The reaction liquid was concentrated under reduced pressure, diluted with diethyl ether, washed with a saturated sodium hydrogen carbonate aqueous solution and a saturated sodium chloride aqueous solution in sequence, dried over anhydrous magnesium sulfate, and then concentrated conducted under reduced pressure. The obtained residue was purified by silica gel column chromatography to give 0.282 g of ethyl (2-methylene-3,4-(dimethylmethylenedioxy)-5-(1-ethoxyethoxy)cyclohexylidene)acetate having the following property.

FD mass spectrum: [M]+340.

EXAMPLE 33

Ethyl (2-methylene-3,4-(dimethylmethylenedioxy)-5-(1-ethoxyethoxy)cyclohexylidene)acetate was dissolved in 5 ml of ethanol, and a catalytic amount of pyridinium p-toluenesulfonate was added, followed by stirring at room temperature for 15 minutes. A sodium hydrogen carbonate aqueous solution was added to the reaction mixture, and extraction was conducted with diethyl ether. The extract was washed with a saturated sodium chloride aqueous solution, dried over anhydrous magnesium sulfate, and concentrated under reduced pressure. The obtained residue was purified by silica gel column chromatography to afford 0.202 g of ethyl (2-methylene-3,4-(dimethylmethylenedioxy)-5-hydroxycyclohexylidene)acetate having the following property.

FD mass spectrum: [M]+268

EXAMPLE 34

Ethyl (2-methylene-3,4-(dimethylmethylenedioxy)-5-hydroxycyclohexylidene)acetate (0.268 g) was dissolved in 5 ml of methylene chloride, and 0.204 g of imidazole and 0.30 g of tert-butyldiphenylsilyl chloride were added, followed by stirring the mixture at room temperature for 3 hours. The reaction mixture was poured into water, and extracted with diethyl ether. The extract was washed with a saturated sodium chloride aqueous solution, dried over anhydrous magnesium sulfate, and concentrated under reduced pressure. The obtained residue was purified by silica gel column chromatography to give 0.450 g of ethyl (2-methylene-3,4-(dimethylmethylenedioxy)-5-(tert-butyldiphenylsilyloxy)cyclohexylidene) acetate having the following property.

FD mass spectrum: [M]+506.

EXAMPLE 35

Ethyl (2-methylene-3,4-(dimethylmethylenedioxy)-5-(tert-butyldiphenylsilyloxy)cyclohexylidene)acetate (0.506 g) was dissolved in 10 ml of ethanol, and a catalytic amount of p-toluenesulfonic acid was added, followed by stirring the mixture at room temperature for 5 hours. Water was added to the reaction mixture, and extraction was conducted with diethyl ether. The extract was washed with a saturated sodium chloride aqueous solution, dried over anhydrous magnesium sulfate, and concentrated under reduced pressure. The obtained residue was purified by silica gel column chromatography to give 0.405 g of ethyl (2-methylene-3,4-dihydroxy-5-(tert-butyldiphenylsilyloxy)cyclohexylidene)acetate having the following property.

FD mass spectrum: [M]+466.

EXAMPLE 36

Ethyl (2-methylene-3,4-dihydroxy-5-(tert-butyldiphenylsilyloxy)cyclohexylidene)acetate (0.466 g) was dissolved in 5 ml of methylene chloride, and 0.204 g of imidazole and 0.30 g of tert-butyldiphenylsilyl chloride were added, followed by stirring the mixture at room temperature for 3 hours. The reaction mixture was poured into water, and extracted with diethyl ether. The extract was washed with a saturated sodium chloride aqueous solution, dried over anhydrous magnesium sulfate, and concentrated under reduced pressure. The obtained residue was purified by silica gel column chromatography to give 0.664 g of ethyl (3,5-bis-(tert-butyldiphenylsilyloxy)-4-hydroxy-2-methylene-cyclohexylidene)acetate having the following property.

FD mass spectrum: [M]+704.

EXAMPLE 37

Ethyl (3,5-bis-(tert-butyldiphenylsilyloxy)-4-hydroxy-2-methylenecyclohexylidene)acetate (0.704 g) was dissolved in 20 ml of toluene, and 2.5 ml of a 1N diisobutyl aluminum hydride/hexane solution was added dropwise at −78° C. After stirring for 1 hour, the reaction mixture was poured into cold dilute hydrochloric acid, and extracted with diethyl ether. The extract was washed with a saturated sodium chloride aqueous solution, dried over anhydrous sodium sulfate, and concentrated under reduced pressure. The obtained residue was purified by silica gel column chromatography to afford 511 mg of (3,5-bis-(tert-butyldiphenylsilyloxy)-4-hydroxy-2-methylenecyclohexylidene)ethanol having the following property.

FD mass spectrum: [M]+662.

EXAMPLE 38

(3,5-Bis-(tert-butyldiphenylsilyloxy)-4-hydroxy-2-methylenecyclohexylidene)ethanol (662 mg) was dissolved in 10 ml of methylene chloride, and a catalytic amount of pyridinium p-toluenesulfonate was added. Then, a solution comprising 100 mg of dihydropyran and 1 ml of methylene chloride was added dropwise under ice cooling, and the mixture was stirred at room temperature for 1 hour. The reaction mixture was washed with a sodium hydrogen carbonate aqueous solution, then dried over anhydrous sodium sulfate, and concentrated under reduced pressure. The obtained 4-(tetrahydropyran-2-yloxyethylidene)-2,6-bis-(tert-butyldiphenylsilyloxy)-3-methylenecyclohexanol was dissolved in 10 ml of tetrahydrofuran, and the solution was added dropwise to a 5 ml tetrahydrofuran suspension of 25 mg sodium hydride. After heating at 50° C., 145 mg of allyl bromide was added, and stirring continued overnight. The reaction mixture was poured into ice water, and extracted with diethyl ether. The extract was washed with a saturated sodium chloride aqueous solution, and dried over anhydrous sodium sulfate, and concentrated under reduced pressure. The obtained (4-allyloxy-3,5-bis-(tert-butyldiphenylsilyloxy)-2-methylenecyclohexylidene)ethyl tetrahydropyran-2-yl ether was dissolved in 10 ml of tetrahydrofuran, and 1 ml of a 1N tetrahydrofuran solution of 9-borabicyclo[3,3,1]nonane was added under ice cooling, followed by stirring the mixture at room temperature for 1 hour. Under ice cooling, 1 ml of a 1 N sodium hydroxide aqueous solution and 0.3 ml of a 35% hydrogen peroxide aqueous solution were added, and the mixture was stirred for 1 hour. The reaction mixture was extracted with diethyl ether. The extract was diluted with water, a sodium thiosulfate aqueous solution and a sodium chloride aqueous solution in sequence, dried over anhydrous sodium sulfate, and concentrated under reduced pressure. The obtained residue was purified by silica gel column chromatography to give 427 mg of 3-(4-(tetrahydropyran-2-yloxyethylidene)-2,6-bis-(tert-butyldiphenyl silyloxy)-3-methylenecyclohexyloxy)propan-1-ol.

The thus obtained 3-(4-(tetrahydropyran-2-yloxyethylidene)-2,6-bis-(tert-butyldiphenylsilyloxy)-3-methylene cyclohexyloxy)propan-1-ol (402 mg) was dissolved in 10 ml of methylene chloride, and 68 mg of imidazole was added. Then, 206 mg of tert-butyldiphenylsilyl chloride was added under ice cooling, and the mixture was stirred at room temperature for 3 hours. After the reaction mixture was concentrated, ethanol and dilute hydrochloric acid were added, and stirring was conducted for 1 hour. The reaction mixture was extracted with diethyl ether. The extract was washed with a saturated sodium chloride aqueous solution, dried over anhydrous magnesium sulfate, and concentrated under reduced pressure. The obtained residue was purified by silica gel column chromatography to provide 407 mg of (4-(3-tert-butyldiphenylsilyloxypropoxy)-3,5-bis-(tert-butyldiphenylsilyloxy)-2-methlenecyclohexylidene)ethanol having the following property.

FD mass spectrum: [M]+958.

REFERENTIAL EXAMPLE 15

N-chlorosuccinimide (140 mg) was suspended in 10 ml of methylene chloride, and 74 mg of dimethyl sulfide was added at 0° C. The mixture was stirred, and cooled to −25° C. A solution of 958 mg of (4-(3-tert-butyldiphenylsilyloxypropoxy)-3,5-bis-(tert -butyldiphenylsilyloxy)-2-methylenecyclohexylidene) ethanol in 2 ml of methylene chloride was added dropwise, followed by stirring at 0° C. for 2 hours. A sodium chloride aqueous solution was added to the reaction mixture, and extraction was conducted with diethyl ether. The extract was washed with a sodium chloride aqueous solution, dried over anhydrous sodium sulfate, and then concentrated under reduced pressure. There resulted 931 mg of (4-(3-tert-butyldiphenylsilyloxypropoxy)-3,5-bis-(tert-butyldiphenylsilyloxy)-2-methylenecyclohexylidene)ethyl chloride.

(4-(3-Tert-butyldiphenylsilyloxypropoxy)-3,5-bis-(tert-butyldiphenylsilyloxy)-2-methylenecyclohexylidene)ethyl chloride (870 mg) was dissolved in tetrahydrofuran, and 2 ml of a 0.5N tetrahydrofuran solution of lithium diphenylphosphide was added dropwise at 0° C. Stirring was conducted at room temperature for 1 hour. The reaction mixture was concentrated under reduced pressure. The obtained residue was dissolved in chloroform, and washed with a 5% hydrogen peroxide aqueous solution, a sodium sulfite aqueous solution, dilute hydrochloric acid, a sodium hydrogen carbonate aqueous solution and a saturated sodium chloride aqueous solution in sequence. The organic layer was dried over anhydrous magnesium sulfate, and concentrated under reduced pressure. The obtained residue was purified by silica gel column chromatography to provide 834 mg of (4-(3-tert-butyldiphenylsilyloxypropoxy)-3,5-bis-(tert-butyldiphenylsilyloxy)-2-methylenecyclohexylidene)ethyl diphenylphosphine oxide.

REFERENTIAL EXAMPLE 16

(4-(3-Tert-butyldiphenylsilyloxypropoxy)-3,5-bis-(tert-butyldiphenylsilyloxy)-2-methylenecyclohexylidene) ethyldiphenylphosphine oxide (571 mg) was dissolved in 5 ml of tetrahydrofuran, and 0.5 ml of a 1N butyl lithium/hexane solution was added dropwise at 0° C., followed by stirring the mixture for 15 minutes. A solution comprising 197 mg of 1-(1,5-dimethyl-5-triethylsilyloxy)-2,3,3a,4,5,6,7,7a-octahydroinden-4-one and 2 ml of tetrahydrofuran was added dropwise to the reaction mixture, and the mixture was stirred overnight at room temperature. Chloroform was added to the reaction mixture. The reaction mixture was washed with a sodium hydrogen carbonate aqueous solution and a saturated sodium chloride aqueous solution in sequence, dried over anhydrous magnesium sulfate, and concentrated under reduced pressure. The obtained residue was purified by silica gel column chromatography to provide 507 mg of (2-(3-tert-butyldiphenylsilyloxypropoxy)-1,3-bis-(tert-butyldiphenylsilyloxy)-25-triethylsilyloxy-9, 10-secocholesta-5,7,10(19)-triene.

(2-(3-Tert-butyldiphenylsilyloxypropoxy)-1,3-bis-(tert-butyldiphenylsilyloxy)-25-triethylsilyloxy-9,10-secocholesta-5,7,10(19)-triene was dissolved in 10 ml of tetrahydrofuran, and a tetrahydrofuran solution of tetrabutylammonium fluoride was added. The mixture was stirred at room temperature for 3 hours. The reaction mixture was extracted with diethyl ether. The extract was washed with a saturated sodium chloride aqueous solution, dried over anhydrous magnesium sulfate, and concentrated under reduced pressure. The obtained residue was purified by silica gel column chromatography to provide 172 mg of 2-(3-hydroxypropoxy)-1,25-dihydroxyvitamin D$_3$. The properties of the resulting 2-(3-hydroxypropoxy)-1,25-dihydroxyvitamin D$_3$ coincided with those of the literature [Japanese Laid-open Patent Application (Kokai) No. 107929/1988].

What we claim is:

1. Cyclohexanetriol derivatives represented by formula (I)

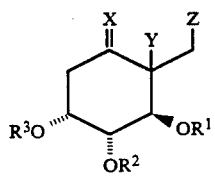

wherein $R^1$, $R^2$ and $R^3$ are the same or different, and each denotes a hydrogen atom or a protecting group of a hydroxyl group, X denotes an oxygen atom, =CHCH$_2$OR$^4$, =CHCHO or =CHCO$_2$R$^5$ Y denotes a hydrogen atom and Z denotes —OR$^6$ or Y and Z together form a single bond; or X and Z together form =NO—, =CHCH(OR$^7$)O— or =CHCO$_2$— and Y is a hydrogen atom, $R^4$ and $R^6$ denote a hydrogen atom or a protecting group of a hydroxyl group respectively, $R^5$ denotes a lower alkyl group, $R^7$ denotes a hydrogen atom or a lower alkyl group.

2. The cyclohexanetriol derivatives of claim 1 wherein the protecting group of the hydroxyl group is an acyl, alkoxycarbonyl, trisubstituted silyl, 1-alkoxyalkyl, 2-oxacycloalkyl or ketal group.

3. The cyclohexanetriol derivatives of claim 1 wherein $R^1$ is a hydrogen atom, or an acetyl, pivaloyl, benzoyl, methoxycarbonyl, ethoxycarbonyl, triethylsilyl, triisopropylsilyl, tert-butyldimethylsilyl, tert-butyldiphenylsilyl, methoxymethyl, methoxyethoxymethyl, 1-ethoxyethyl or tetrahydropyranyl group, $R^2$ is a hydrogen atom, or an acetyl, pivaloyl, benzoyl, methoxycarbonyl or ethoxycarbonyl group, or $R^1$ and $R^2$ together form an isopropylidene group, and $R^3$ is a hydrogen atom, or an acetyl, pivaloyl, benzoyl, methoxycarbonyl, ethoxycarbonyl, triethylsilyl, triisopropylsilyl, tert-butyldimethylsilyl, tert-butyldiphenylsilyl, methoxymethyl, methoxyethoxymethyl, 1-ethoxyethyl or tetrahydropyranyl group.

4. The cyclohexanetriol derivatives of claim 1 wherein $R^1$ is a hydrogen atom, or an acetyl, tert-butyldimethylsilyl or tert-butyldiphenylsilyl group, $R^2$ is a hydrogen atom, or an acetyl or methoxycarbonyl group, or $R^1$ and $R^2$ together form an isopropylidene group, $R^3$ is a hydrogen atom, or an acetyl, methoxymethyl, 1-ethoxyethyl, tert-butyldimethylsilyl or tert-butyldiphenylsilyl group.

5. The cyclohexanetriol derivatives of claim 1 which are represented by formula (IA)

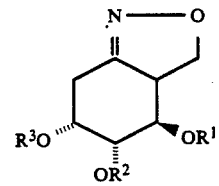

wherein $R^1$, $R^2$ and $R^3$ are as defined in claim 1.

6. The cyclohexanetriol derivatives of claim 1 which are represented by formula (IB) or (IC)

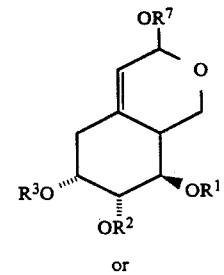

or

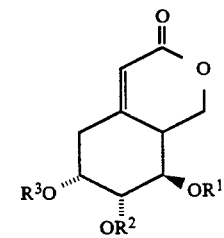

wherein $R^1$, $R^2$, $R^3$ and $R^7$ are as defined in claim 1.

7. The cyclohexanetriol derivatives of claim 1 which are represented by formula (ID) or (IE)

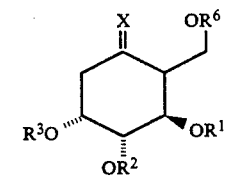

or

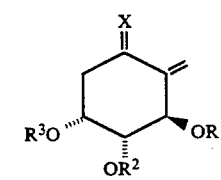

wherein X, $R^1$, $R^2$, $R^3$ and $R^6$ are as defined in claim 1.

8. The cyclohexanetriol derivatives of claim 7 wherein X is =CHCH$_2$OR$^4$, and $R^6$ is a hydrogen atom or a tetrahydropyranyl group.

9. The cyclohexanetriol derivatives of claim 7 wherein $R^6$ is a hydrogen atom or a 1-ethoxyethoxy or tert-butyldimethylsilyl group.

* * * * *